(12) United States Patent
Milne et al.

(10) Patent No.: US 7,592,182 B2
(45) Date of Patent: Sep. 22, 2009

(54) ASSAY (75) Inventors: Ken Milne, Dundee (GB); Margaret Lawlor, Dundee (GB)

(73) Assignee: Axis-Shield Diagnostics Limited (GB)

( * ) Notice: Subject to any disclaimer, the term of this patent is extended or adjusted under 35 U.S.C. 154(b) by 723 days.

(21) Appl. No.: 11/196,212

(22) Filed: Aug. 3, 2005

(65) Prior Publication Data
US 2006/0030050 A1   Feb. 9, 2006

Related U.S. Application Data (60) Provisional application No. 60/598,511, filed on Aug. 3, 2004.

(30) Foreign Application Priority Data

| Aug. 3, 2004 | (GB) | ................................ 0417212.8 |
| Apr. 20, 2005 | (GB) | ................................ 0507955.3 |

(51) Int. Cl.
   *G01N 33/72* (2006.01)
   *G01N 33/558* (2006.01)
(52) U.S. Cl. .......................... 436/67; 436/66; 436/514; 436/536; 436/161; 436/166
(58) Field of Classification Search .................. 436/67, 436/536, 66, 514, 161, 166
   See application file for complete search history.

(56) References Cited

U.S. PATENT DOCUMENTS

| 4,658,022 A | 4/1987 | Knowles et al. |
| 5,242,842 A * | 9/1993 | Sundrehagen ................ 436/536 |
| 5,506,144 A * | 4/1996 | Sundrehagen ................ 436/66 |
| 5,736,349 A | 4/1998 | Sasaki et al. |
| 5,786,428 A | 7/1998 | Arnold et al. |

FOREIGN PATENT DOCUMENTS

| EP | 0 315 866 A1 | 5/1989 |
| EP | 1 314 982 A1 | 5/2003 |
| WO | 91/09678 | 7/1991 |
| WO | 97/26864 | 7/1997 |
| WO | 98/51435 A | 11/1998 |
| WO | 02/086512 A2 | 10/2002 |

OTHER PUBLICATIONS

Arthur Arnone et al., *The Binding of Zinc to Human Deoxyhemoglobin and Its Possible Relevance to the Anti-Stickling Effect of Zinc*, Progress in Clinical and Biological Research, 1977, vol. 14, pp. 317-328.

(Continued)

*Primary Examiner*—Walter D Griffin
*Assistant Examiner*—Christine T Mui
(74) *Attorney, Agent, or Firm*—DLA Piper LLP (US)

(57) ABSTRACT

Compositions and assay methods for and relating to the detection of glycated hemoglobin are provided. In particular, the presence and level of glycated hemoglobin can be detected in a blood sample. The compositions comprise microparticles which have zinc coating for use in the improved binding of proteins exhibiting a zinc binding domain, in particular glycated hemoglobin.

30 Claims, 2 Drawing Sheets

OTHER PUBLICATIONS

Joseph M. Rifkind et al., *Interaction of Zinc with Hemoglobin: Binding of Zinc and the Oxygen Affinity*, Biochemistry, Oct. 4, 1977, vol. 16, No. 20, pp. 4438-4443.

John G. Gilman et al., *The Oxgen-Linked Zinc-Binding Site of Human Haemoglobin*, The Biochemical Journal, Mar. 1, 1978, vol. 169, No. 3, pp. 625-632.

John J. Cunningham, *Hyperzincuria in Individuals with Insulin-Dependent Diabetes Mellitus: Concurrent Zinc Status and the Effect of High-Dose Zinc Supplementation*, Metabolism: Clinical and Experimental, Dec. 1994, vol. 43, No. 12, pp. 1558-1562.

Abudiab, T. et al.; "Preparation of magnetic immobilized metal affinity separation media and its use in the isolation of proteins"; Journal of Chromatography A, 795 1998; pp. 211-217.

Hutchens, T. W., et al.; "Ligand-binding Properties of Estrogen Receptor Proteins after Interaction with Surface-immobilized Zn(II) Ions: Evidence for Localized Surface Interactions and Minimal Conformational Changes"; Journal of Molecular Recognition, vol. 3, N. 4, 1990, pp. 174-179.

Gupta, M. N., et al.; "Immobilized Metal Affinity Chromatography without Chelating Ligands: Purification of Soybean Trypsin Inhibitor on Zinc Alginate Beads"; Biotechnol Prog. 2002, 18, pp. 78-81.

Plunkett, S. D. et al.; "Molecularly imprinted polymers on silica: selective supports for high-performance ligand-exchange chromatography"; Journal of Chromatography A, 708, (1995; pp. 19-29.

Delbeck g., et al.; "Hämolyse and Hämoglobinadsorption durch Zinkverbindugen"; Res. Exp. Med., vol. 160, 1973, pp. 255-260.

\* cited by examiner

ASSAY

CROSS REFERENCE TO RELATED APPLICATION

This application claims the benefit of U.S. provisional patent application Ser. No. 60/598,511, filed on Aug. 3, 2004, the entire disclosure of which is herein incorporated by reference.

TECHNICAL FIELD

The disclosure relates to assay methods for the detection of glycated hemoglobin A1c (HbA1c). Specifically, the disclosure relates to microparticles having zinc coating for use in the binding of proteins exhibiting a zinc binding domain and in particular hemoglobin, such as glycated hemoglobin.

BACKGROUND

Hemoglobin (Hb) is the protein present in red blood cells which is responsible for the transportation of oxygen. Hemoglobin occurs in several variants, the most common form being hemoglobin A which comprises about 90% of the total hemoglobin found in blood.

A1c is a specific subtype of hemoglobin A. HbA1c is a glycated form of hemoglobin which is formed by the non-enzymatic glycation of the N-terminal valine group of the hemoglobin (Ao) beta chain. In a non-diabetic individual, around 90% of their total hemoglobin is present in a non-glycated form (hemoglobin Ao).

Proteins in solution in body fluids are continually subject to glycation processes. Glucose binds slowly to hemoglobin A to form the A1c glycated subtype. The formation of HbA1c reaches a steady state with about 3.0% to 6.5% of hemoglobin being of the A1c subtype. Most diabetic individuals have a higher blood glucose level than non-diabetics. This results in a higher HbA1c level in diabetic patients, with type 1 (juvenile) and type 2 (adult onset) diabetes sufferers having a HbA1c level ranging from about 6% to 15%.

Diabetes mellitus is a disease associated with poor glycemic control. Diabetes related complications may be reduced by long term monitoring and tight control of blood glucose levels. In the diabetic patient where blood glucose levels are obviously elevated, the HbA1c level can also increase.

The quantification of an individual's HbA1c level can act as an indicator of the average recent blood glucose level, which can in turn indicate the possible level of glycation damage to tissues, and thus the likelihood of possible associated diabetic complications if this state remains for the long term.

The HbA1c test is well established as a good index for an individual's glycemic control. The HbA1c test (which is also known as the hemoglobin A1c test, the glycated hemoglobin A1c test, the glycohemoglobin A1c test or the A1c test) is a laboratory based assay which reveals the average blood glucose level over a period of two to three months. The test measures the number of glucose molecules attached to hemoglobin. As erythrocytes are recycled after their normal lifetime of around 90 to 120 days, the measurement of the attached glucose in a current blood sample allows average blood sugar levels over the previous 2 to 3 months to be determined.

The use of the HbA1c test to monitor longer term glucose levels serves to complement the continuous day to day monitoring of blood glucose levels which can be performed directly by an individual determining their glucose concentration in blood, plasma or urine.

The monitoring of HbA1c levels is currently one of the best ways to monitor diabetes mellitus in order to assess whether the condition is being properly controlled (see, e.g., DCCT clinical study conducted from 1983 to 1993 by the National Institute of Diabetes and Digestive and Kidney Diseases). Specifically, the test allows a physician to ensure that diabetic patients are achieving optimal glycemic control and further ensures that diabetic patients are properly controlling their glucose levels between physician check ups.

It is recommended that all individuals with type 2 diabetes should have an HbA1c test at least twice a year. In cases where the resulting blood glucose level is too high, a repeat test at more frequent intervals is recommended. This testing results in around 40 million tests being conducted each year in Europe and the US alone.

Regular assessment of HbA1c levels allows an individual to manage their condition, this resulting in the delay or prevention of serious eye, kidney and nerve disease in people with diabetes. There is also an associated improvement in the general health of the individual.

Current methods used to measure HbA1c levels include column chromatography on ion exchange or affinity resins and high performance liquid chromatography (HPLC). However, none of these methods are ideal as methods for measuring HbA1c levels as they suffer from a number of drawbacks, such as not being accurate or easily standardized, being expensive and/or involving complicated procedures.

There accordingly exists a need for a fast, reliable and easy to use method for the accurate detection of HbA1c levels.

SUMMARY

It has been now surprisingly found that a microparticle coated with zinc exhibits improved binding of target proteins bearing a zinc binding domain, particularly hemoglobin and derivatives such as glycated hemoglobin. Thus, these microparticles can be used in methods for the detection of glycated hemoglobin levels and further for the isolation of proteins or other molecules which exhibit at least one zinc binding site.

We thus provide an assay method for the determination of the level of glycated hemoglobin within a sample. In the method, a sample containing hemoglobin is provided, and the hemoglobin is extracted from the sample and partially denatured. The extracted hemoglobin is exposed to microparticles coated with zinc, in order to allow binding of hemoglobin and glycated hemoglobin to the microparticles. The amount of HbA1c in the sample can then be determined.

We also provide an assay method for the in vitro diagnosis and monitoring of diabetes mellitus through the assessment of HbA1c glycated hemoglobin levels. In the method, a sample comprising hemoglobin is obtained from an individual. The sample is hemolysed to release cell bounded hemoglobin and the hemoglobin is partially denatured. Glycated hemoglobin is captured on microparticles coated with zinc, either before, during or after exposing the sample to signal generating molecules capable of binding to the glycated hemoglobin present in the sample. Any unbound signal generating are removed, and the amount of bound signal generating molecules is measured to determine the percentage level of HbA1c present in the sample.

We also provide a method of isolating hemoglobin from a biological sample. In the method, a biological sample from a patient is provided, and hemoglobin in the sample is captured on microparticles which are pre-coated with zinc The bound hemoglobin can then be eluted from the zinc coated microparticle.

We also provide an assay for the selective binding of at least one target protein comprising a zinc binding site. In the method, a sample is provided and exposed to zinc coated microparticles. Target proteins are captured on the zinc coated microparticles, and the microparticles are isolated. The presence of target proteins bound to the microparticles can then be detected and optionally purified from the microparticles.

We also provide a kit for the performance of the methods. The kit can comprise microparticles, together with instructions (including protocols) for the performance of the assay methods.

We also provide a microparticle coated with zinc molecules.

DETAILED DESCRIPTION OF THE INVENTION

Figure 1:
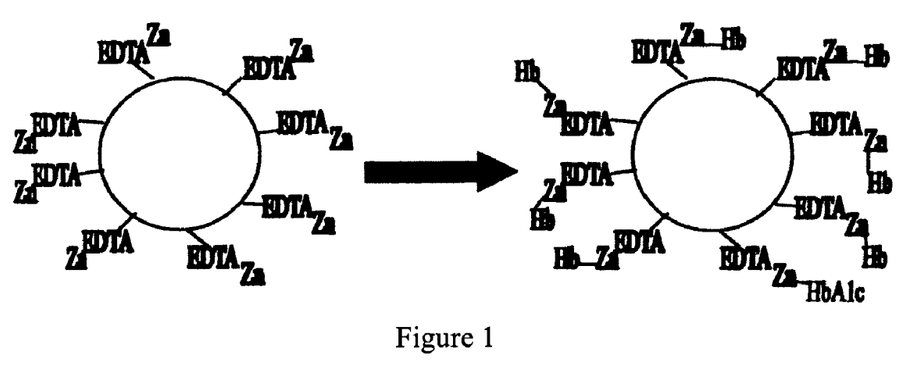
FIG. 1 shows an illustrative example of the capture of hemoglobin ("Hb") and glycated hemoglobin subtype HbA1c and zinc ("Zn") coated microparticles, the zinc being bound to the microparticle by an EDTA intermediate.
Figure 2:
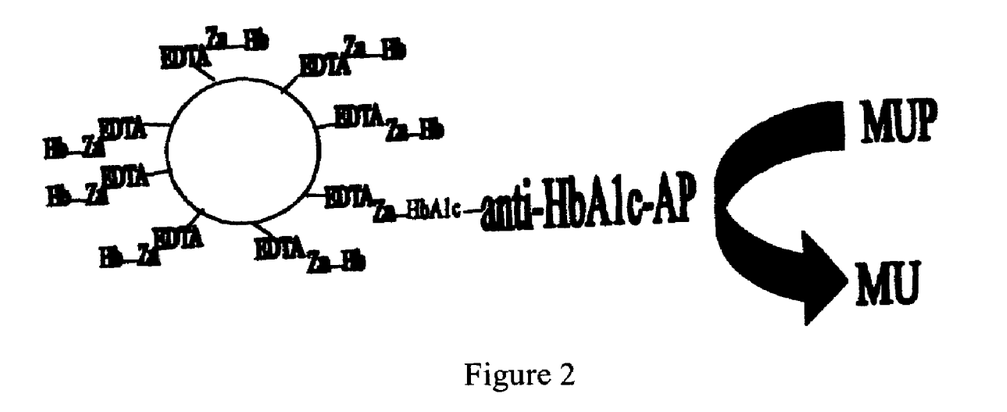
FIG. 2 shows a preferred method for the detection of a bound target protein, in this case glycated hemoglobin subtype HbA1c, following the binding of the microparticle.

Compositions and assay methods for the detection of hemoglobin in a sample are provided. In particular, the presence and level of hemoglobin (also sometimes represented herein as "Hb") can be detected in a blood sample. The present compositions comprise microparticles which have zinc coating, for use in the binding of proteins exhibiting a zinc binding domain, in particular glycated hemoglobin, for example glycated hemoglobin A1c (HbA1c).

We thus provide an assay method for the determination of the level of glycated hemoglobin within a sample, the method comprising the steps of providing a sample which comprises hemoglobin;

extracting the hemoglobin from the sample and partially denaturing the hemoglobin present;

exposing the hemoglobin to microparticles coated with zinc in order to allow binding of hemoglobin and glycated hemoglobin (e.g., HbA1c) to the microparticles; and determining the amount of glycated hemoglobin in the sample.

In the practice of the disclosure, the sample can comprise blood, in particular human anti-coagulated whole blood. The sample can also comprise red blood cell pellets, blood hemolysates or blood extracts such as serum. The sample can also be collected on filter paper, dried and then redissolved. Techniques for the collection of a sample comprising hemoglobin are within the skill in the art, and include biopsy, skin or cell scrapings, and the drawing of blood, serum or other bodily fluids with a lancet or through a hypodermic needle. Samples for use can comprise human anti-coagulated whole blood, red blood cell pellets, blood hemolysates or blood extracts.

In the practice of the disclosure, the hemoglobin can be obtained by hemolysis of the sample in order to release the cell bounded hemoglobin. This step is particularly desirable where the blood sample comprises whole blood or red blood cells. The blood sample can be hemolyzed by techniques which are well known to those skilled in the art, for example by adding hemolysis agents such as saponin, sodium dodecyl sulphate (SDS) and/or quarternary ammonium salts. Hemolysis to be performed using heat. The methods described herein also can optionally include the step of purifying hemoglobin from a sample. The hemoglobin need not be glycated.

Partial denaturation of the hemoglobin during the treatment step can be performed using detergents. An optimized combination of detergents can be formulated in order to effect the preferred degree of denaturation of the hemoglobin. Suitable detergents include cholate, N-octyl-glucoside, N-octyl-thioglucoside, triton X, zwittergent3-14 and bile salts. Without wishing to be bound by any theory, it is believed that the importance of denaturing the hemoglobin is accorded to the fact that this results in a conformational change in the hemoglobin molecule. This conformational change is believed to facilitate and permit high affinity binding of zinc to the hemoglobin molecule. The occurrence of high affinity binding is advantageous, as it permits the zinc and hemoglobin to remain in an associated bound state during any washing step or steps which may be performed during assay methods.

The method can further comprise the step of removing cell debris by centrifugation, immediately following the hemolysis of the sample.

Again without wishing to be bound by any theory, it is believed that the denaturation of the hemoglobin provides for the formation or exposure of a binding site which permits binding to zinc molecules, for example high affinity binding to zinc molecules, while at the same time retaining an epitope to which an antibody or similar binding member can bind in order to indicate the presence of the hemoglobin.

In the practice of the disclosure, the sample can be first hemolyzed before the hemoglobin contained therein is partially denatured.

The step of exposing the hemoglobin to the zinc coated microparticles can be performed at a pH of between about pH 6 and about pH 8, for example about pH 7.

Suitable microparticles for use can comprise a bead such as a latex bead, silica bead, chelating sepharose bead or a magnetic bead. For example, carboxyl groups may be provided on the surface of the latex bead in order to facilitate the attachment of zinc molecules. As an alternative, silica beads may be used. Silica beads are however generally heavier than latex beads. Where the microparticle is silica, it can have a diameter of about 10 to about 50 micrometers, for example, about 20 to about 30 micrometers. The silica particle can be hollow or substantially hollow, in order to reduce its density.

The microparticle can comprise dextran or polyethylene glycol (PEG). Where the microparticle comprises dextran, it can form a dextran backbone.

Suitable silica bead microparticles are commercially available from Micromod Partikeltechnologie. Germany under the product name SICASTAR™ beads. Such beads can comprise EDTA as a chelator. For example, the SICASTAR™ bead with an EDTA surface coating, a size of 1.5 µm and a solid content of 50 mg/ml, this having the Micromod catalogue code 43-12-153, is suitable for use in the present methods. Alternatively the bead can be a SICASTAR™ bead with an EDTA surface coating, a size of 1 µm and a solid content of 50 mg/ml, this having a Micromod catalogue code of 43-12-103. Further, the beads can be a SICASTAR™ bead with an EDTA surface coating, a size of 500 um and a solid content of 50 mg/ml, this having a catalogue code of 43-12-502, or a SICASTAR™ bead with an EDTA surface coating, a size of 300 um and a solid content of 50 mg/ml, this having a catalogue code of 43-12-502, or Sicastar™ bead with an EDTA surface coating, a size of 300 nm and a solid content of 50 mg/ml, this having a catalogue code of 43-12-302.

Suitable latex bead microparticles can also be obtained from Micromod Partikeltechnologie, Germany under product code 01-121-53. A magnetic form of the latex bead is available under Micromod catalogue number 01-461-53. Other suitable magnetic bead microparticles can be obtained from Scipac Ltd, Kent, UK.

Techniques for the binding of metals (such as zinc) onto microparticle surfaces are within the skill in the art. For example, metal ions can be bound to a microparticle surface by complexing with chelators which are associated with the microparticle surface, by inclusion into pores of the particles, by adhesion processes or by electrostatic interactions. Both magnetic and non-magnetic microparticles can be used in the performance of the present methods. The zinc can also be deposited on the surface by vacuum deposition.

As described above, a chelator can be bound to the surface of the microparticle, the chelator allowing zinc molecules to be conjoined thereto. Advantageously, the chelator can serve to space the bound zinc molecule away from the surface of the microparticle, when in a bound state.

The chelator can comprise any suitable zinc binding chelating agent. Suitable chelators include ethylenediamine tetraacetic acid (EDTA), trisodium calcium diethylenetri-amin-pentaacetate (DTPA), disodium calcium cyclohex-anediaminetetraacetate (CDTA), sodium calcium edetate, DMSA and DMPS. Other suitable chelating agents include Ethylenediamine (EDA), Diethylenetriamine (DETA) and Aminoethylethanolamine (AEEA) ethyleneamines, and any other chelator having zinc-complexing properties.

In the practice of the disclosure, the zinc coating can serve to activate the microparticle. Zinc chloride can be used to coat the microparticles, although any suitable zinc salt or elemental form of zinc (including zinc ions) can be used to coat the surface of the microparticle.

The microparticle can comprise a bead such as a polystyrene bead, silica bead, chelating sepharose bead or a magnetic bead. The microparticle can also comprise a chelating bead which is activated by a pre-charged zinc particle.

Without wishing to be bound by theory, it is believed that the microparticle will not necessarily be completely covered by the bound zinc molecule. However there can be a high level of bound zinc molecules on the microparticle in relation to the available microparticle surface area; for example, there can be at least about 30%, at least about 40%, at least about 50%, at least about 60%, at least about 70%, at least about 80%, at least about 90%, at least about 95%, or at least about 99% bound zinc molecules on the microparticle in relation to the available microparticle surface area.

Advantageously, it has been found that the zinc bound microparticle has improved properties in the binding of hemoglobin, its related derivatives and glycated forms. Without wishing to be bound by any theory, this advantage is believed to be due to the advantageous surfactant properties provided by the present compound. Again, without wishing to be bound by theory, it is believed that the improved surfactant properties exhibited by the present compound allow hemoglobin to be more efficiently extracted from a membrane bounded state, by conferring improved washing conditions and allowing fast and efficient rupture of the cell membrane to occur, and, thereafter, efficient hemoglobin binding.

Following binding of hemoglobin to the microparticles of the present invention, the determination of the amount of glycated hemoglobin, such as HbA1c, present in a sample can be performed. Analysis for glycated hemoglobin can be carried out on any hemoglobin source, e.g. hemolyzed erythrocytes, which has been subjected to the present methods. Such an anlysis can be performed by any suitable technique, such as an immunoassay; e.g., competitive or immunometric assay types. Examples of the latter type include radioimmunometric assays (IRMA) and enzyme linked immunosorbent assays (ELISA). In a competitive assay the antigen (i.e. the glycated hemoglobin) can be labelled with a detectable label. The sample containing the antigen can be incubated with the glycated hemoglobin-specific antibody and the labelled antigen, and after formation of immune complexes, separation and detection, the level of glycated hemoglobin in the sample can be determined.

Any suitable technique for detecting glycated hemoglobin can be used in the practice of the present methods, including contacting the glycated hemoglobin with signal-generating molecules which selectively bind to glycated hemoglobin to label it and make it detectable. Suitable signal generating molecules include direct labels, enzyme labels or radiolabels which can, for example, bind selectively to glycated hemoglobin, but not to non-glycated hemoglobin. Such signal generating molecules can be bound to glycated hemoglobin by means of a specific binding partner such as an antibody; for example, a monoclonal antibody or boronic acids. The signal generating molecule can also be conjugated to the antibody.

One way in which an antibody can be detectably labelled is by conjugating it to an enzyme. This enzyme, in turn, when later exposed to its substrate, can catalyze a reaction with the substrate such that a detectable chemical moiety results. Such detectable chemical moieties can be detected for example, by spectrophotometric or fluorometric means (e.g., ELISA system).

Examples of enzymes that can be used as detectable labels include horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

Where the enzyme conjoined to the antibody comprises alkaline phosphatase, and the substrate can be 4-Methylumbelliferyl Phosphate, and the alkaline phosphatase labelled conjugate catalyzes the removal of the phosphate group from the substrate, yielding the fluorescent product 4-Methylumbelliferyl Phosphate. The amount of fluorescence produced is directly linked to the percentage of glycated hemoglobin, such as HbA1c, present in the sample, which can be determined by reference to a standard response curve according to techniques within the skill in the art.

Conveniently, the amount of fluorescence produced can be measured by the MEIA optical assembly. Fluorescence values can be converted to percentages of HbA1c of total hemoglobin by means of a standard curve obtained by plotting the fluorescence at 448 nm, of samples containing known percentages of HbA1c as determined by HPLC or some other suitable measurement.

For increased sensitivity in the ELISA system, the method can further comprise the step of using biotinylated antibody reacting with avidin-peroxidase conjugates. Other techniques for detecting biotinylation can also be used. Such techniques will be apparent to the person skilled in the art, and include detection systems involving streptavidin, systems including peroxidase and alkaline phosphatase detecting systems.

The amount of antigen can also be determined by labelling the antibody with a radioactive isotope. The presence of the radioactive isotope would then be determined by such techniques as are within the skill in the art, such as the use of a gamma counter or a scintillation counter. Isotopes which are particularly useful in this regard are $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$We, $^{75}$Se, $^{111}$In, $^{99m}$Tc, $^{67}$Ga, and $^{90}$Y.

Determination of the antigen can also be performed by labelling the antibody with a fluorescent labelling compound (sometimes herein also called a "dye"). When the fluorescently labelled molecule is exposed to light of the proper wavelength, its presence can then be detected due to fluorescence of the dye. Suitable fluorescent labelling compounds include fluorescein isothiocyanate, rhodamine, phycoerythrin, phycocyanin, allophycocyanin, o-phthaldehyde, and fluorescamine.

Fluorescence emitting metal atoms such as Eu (europium), and other lanthanides, can also be used. These can be attached to the desired molecule by techniques known to those skilled in the art, for example, by means of metal chelating groups, such as DTPA or EDTA.

Another way in which an antibody can be detectably labelled is by coupling it to a chemiluminescent compound. The presence of the chemiluminescent-tagged immunoglobulin can then be determined by detecting the presence of luminescence that arises during the course of a chemical reaction. Suitable chemiluminescent labelling compounds include luminol, isoluminol, aromatic acridinium ester, imidazole, acridinium salt, and oxalate ester.

Likewise, a bioluminescent compound can also be used as a label. Bioluminescence is a special type of chemiluminescence which is found in biological systems, wherein a catalytic protein increases the efficiency of the chemiluminescent reaction. The presence of a bioluminescent molecule can be determined by detecting the presence of luminescence. Suitable bioluminescent labelling compounds include luciferin, luciferase, and aequorin. Chemiluminescent substrates for HRP and alkaline phosphatase can also be used.

The measurement of bound hemoglobin can be also be quantified using UV absorbers in resins such as resorcinol.

In order to ensure that the greatest proportion of glycated hemoglobin in the sample interacts with the signal generating molecules, it is advantageous to use an excess of signal-generating molecules. For example, substantially all glycated hemoglobin contained in the sample can be bound by signal-generating molecules, and thus, be detectable and distinguishable from non-glycated hemoglobin.

The method can further comprise the step of separating the fraction of the signal generating molecules which is not bound to glycated hemoglobin when contacted with the sample.

We also provide an assay method for the in vitro diagnosis and monitoring of diabetes mellitus through the assessment of glycated hemoglobin levels, the method comprising the steps of:
  providing a sample obtained, from an individual which contains hemoglobin;
  hemolysing the sample to release cell bounded hemoglobin and partially denaturing the hemoglobin;
  capturing the glycated hemoglobin on microparticles coated with zinc;
  exposing the sample to signal generating molecules capable of binding to the glycated hemoglobin present in the sample;
  removing signal generating molecules not bound to glycated hemoglobin; and
  quantifying the amount of bound signal generating molecules to determine the percentage level of glycated hemoglobin present in the sample.

As above, the blood sample can comprise human anti-coagulated whole blood, red blood cell pellets, blood hemolysates or blood extracts. The blood sample can be collected by standard techniques. The blood sample can also be places, for example, on filter paper, dried and subsequently redissolved before being subjected to the present assay methods.

Hemolysis of the blood sample and partial denaturation of hemoglobin can be performed as described above.

As above, the sample can first be hemolyzed before partial denaturation of the hemoglobin occurs, or partial denaturation of the hemoglobin can occur concurrently with the hemolysis of the sample.

The step of capturing the hemoglobin upon the zinc coated microparticles can be performed as described above.

Also as above, the method can further comprise the step of removing cell debris by centrifugation, immediately following the hemolysis of the blood sample.

The method can further comprise determining the percentage level of glycated hemoglobin, such as HbA1c, present in the sample through the steps of:
  capturing the microparticles on a suitable base medium;
  washing the microparticles to remove unbound material;
  labelling the glycated hemoglobin with a signal generating molecule being a monoclonal antibody specific for glycated hemoglobin, the monoclonal antibody preferably having a label conjugated thereto; and
  determining the percentage of glycated hemoglobin present in the sample.

The base medium can comprise a glass fiber matrix.

A suitable monoclonal antibody specific for glycated hemoglobin RbA1c can comprise an anti-HbA1c antibody. The anti-HbA1c monoclonal antibody can have an epitope specific for the monosaccharide containing N-terminal 8 amino acids of HbA1c.

The enzyme conjugated to the antibody can be an alkaline phosphatase.

As described above, the monoclonal antibody used to detect glycated hemoglobin can be labelled with an enzyme. The enzyme can comprise alkaline phosphatase, said alkaline phosphatase catalyzing the removal of a phosphate group present in a substrate. The enzyme conjoined to the antibody serves to react with components of a substrate introduced about the bound microparticles, in order to produce a signal which can be measured to determine the percentage of glycated hemoglobin, such as HbA1c, present in a sample.

We further provide assay systems and screening methods for determining HbA1c glycated hemoglobin levels. As used herein, an "assay system" is understood to encompass all components required for performing and analyzing results of an assay that can detect and/or measure a particular event or events.

A variety of assays to detect the activity of proteins that have specific binding activity are available, and known to those skilled in the art. Exemplary assays use fluorescence polarisation and laser scanning techniques to measure binding of fluorescently labelled proteins, peptides or other molecules (See, e.g., Lynch, B. A et al. 1999. Anal Biochem 275:62-73; Li H Y, 2001, J Cell Biochem 80:293-303; and Zuck P et al., Proc Natl Acad Sci USA 1999, 96: 11122-11127, the entire disclosures of which are herein incorporated by reference).

In another example, binding activity can be detected using the scintillation proximity assay (SPA), which uses a biotinylated peptide probe captured on a streptavidin coated SPA bead and radio-labeled partner molecule. The assay specifically detects the radio-labelled protein bound to the peptide probe via scintillant immobilized within the SPA bead (See, e.g., Sonatore L M et al., 1996, Anal Biochem 240:289-297, the entire disclosures of which are herein incorporated by reference).

Suitable screening assays include high throughput or ultra high throughput assays, which can provide automated, cost-effective means of screening.

The assay can be automated and allow between about 40 to about 60 tests to be performed in an hour. The automation could also allow, for example, between about 100 to about 160 tests to be performed per hour. Assays allowing greater or lesser numbers of tests to be performed per hour are also contemplated.

Screening can also be performed using an automated analyzer; for example, the automated AXSYM™ system of Abbott Laboratories. Techniques used for automated sample analysis and throughput include Abbott IMX™ and microparticle enzyme immunoassay, and other techniques known to those skilled in the art.

We also provide a method of isolating hemoglobin from a biological sample, the method comprising the steps of:
providing a biological sample from a patient;
capturing the hemoglobin on microparticles which are pre-coated with zinc; and
eluting the bound hemoglobin from the zinc coated microparticle.

The method further comprises the step of hemolysing the sample and partially denaturing the hemoglobin present in the sample prior to the capturing step.

Hemoglobin obtained by the method includes hemoglobin, derivatives and analogues and in particular glycated forms of hemoglobin such as glycated subtype HbA1c.

We also provide an assay for the selective binding of at least one target protein comprising a zinc binding site, the method comprising the steps of:
providing a sample;
exposing the sample to zinc coated microparticles in accordance with the disclosure;
capturing the target proteins on the zinc coated microparticles;
isolating the microparticles;
detecting the presence of target proteins bound to the microparticles; and
optionally purifying the target protein from the microparticles.

The sample can comprise a biological sample, for example a blood sample, as described above.

We further provide a method comprising the stop of selectively binding zinc coated microparticles to a target protein bearing a zinc binding domain.

Suitable target proteins include hemoglobin and its associated glycated forms, analogues and derivatives thereof, metalloproteases, metallopeptidases, enzymes (e.g., alkaline phosphatases), metallothioneins (MTs) and transcription factors which exhibit or define zinc binding domains.

We also provide a kit for the performance of the methods of the disclosure. The kit can comprise microparticles together with instructions (including protocols) for the performance of the assay methods.

Advantageously, the kit provides instructions for the performance of the methods using the AXSYM™ automated assay system commercially available and provided by Abbott Laboratories (US).

We also provide a microparticle coated with zinc molecules. Microparticles are as described above.

The microparticle can be a chelating bead which is activated by a pro-charged magnetic zinc particle.

We also provide a compound for use in the targeted binding of proteins comprising a zinc binding site, comprising a microparticle coated with zinc molecules.

In the practice of the methods, the zinc coated microparticles can be used in the capture and detection of zinc binding proteins or can be used for the purification of target proteins exhibiting zinc binding domains.

We further provide a compound for use in the improved binding of glycated hemoglobin, comprising a microparticle coated with zinc.

EXAMPLES

The present disclosure will now be described with reference to the following examples which are provided for the purpose of illustration and are not intended to be construed as being limiting on the present disclosure.

Example 1

AXSYM™ Automated Assay Conditions

Manually lysed blood with lysis buffer supplemented with 0.5% TX-100 and 0.8 mM zwittergent 3-14.

Pre-washed tab with MEIA+5% BSA.

Mixed lysed blood sample with equal volume zinc coated EDTA silica microparticles in 30% sucrose and incubated for 5 minutes.

Transferred to tab and washed with MEIA.

Added 1 g/ml αHbA1c in blocking buffer 17 and incubated for 5 minutes.

Washed with MEIA.

Added α-mouse-alkaline phosphatase diluted 1 in 3000 with HEPES pH7.

Washed with MEIA.

Added MUP and read.

TABLE 1

| Sample | Blank | Rate | Ratio |
| --- | --- | --- | --- |
| 1 mg/ml Hb | 175 | 312 | 1:1.8 |
| RBC (5% HbA1c) | 211 | 371 | 1:1.8 |
| RBC (9% HbA1c) | 211 | 531 | 1:2.5 |

The assay detected presence of HbA1c and discriminated between 5% and 9% HbA1c levels.

Example 2

IMX™ Automated Assay Conditions

Pre-washed tab with MEIA+5% BSA.

Mixed sample and 0.1% zinc coated EDTA silica microparticles in 30% sucrose (1:1).

Applied to tab and washed with MEIA (2×50 μl).

Added 1 μg/ml αHbA1c in HEPES and incubated for 5 min.

Washed with MEIA (2×50 μl).

Added α-mouse-alkaline phosphatase conjugated (diluted 1 in 3000 with HEPES) and incubated for 5 min.

Washed with MEIA (2×50 μl).

Added MUP and read.

TABLE 2

| Sample | Rate |
| --- | --- |
| Particles (blank) | 97 |
| HbA1c (0.25 mg) | 330 |
| Hb (0.125 mg) + HbA1c (0.125 mg) | 175 |
| Hb (0.2 mg) + HbA1c (0.05 mg) | 132 |
| Hb (0.25 mg) | 121 |

Increasing the concentrations of HbA1c resulted in higher rates measured.

Example 3

96 Well Vacuum Manifold Assay

Capturing Hb Using Zn Microparticles

Silica EDTA and polystyrene NTA microparticles were coated with $ZnCl_2$ and incubated at 0.5% solids with Hb (0.5 mg/ml) or (0.2 mg/ml) for 10 min. Binding was assessed by measuring the unbound material using OD 405 nm. The readings for 0.5 mg/ml and 0.2 mg/ml fell within the linear range for Hb measurement at 405 nm.

TABLE 3

Binding capacity of zinc coated silica EDTA and polystyrene NTA microparticles for hemoglobin.

| | Measured unbound 0.5 mg/ml Hb Average OD 405 nm (minus background) | Bound (%) | Measured unbound 0.1 mg/ml Hb Average OD 405 nm (minus background) | Bound (%) |
| --- | --- | --- | --- | --- |
| polystyrene NTA | 0.249 | 70 | 0.024 | 84 |
| Silica EDTA 1.5 μm (1st batch) | 0.118 | 86 | 0 | 100 |
| Silica EDTA 1.0 μm | 0.093 | 89 | 0 | 100 |
| Silica EDTA 1.5 μm (2nd batch) | 0.111 | 87 | 0 | 100 |
| Silica EDTA 3.0 μm | 0.273 | 67 | 0.037 | 75 |
| Input Hb 0.5 mg/ml | 0.828 | | | |
| Input Hb 0.1 mg/ml | 0.146 | | | |

This experiment showed that the silica EDTA beads of 1-1.5 μm displayed the highest binding capacity (over 85% for 0.5 mg/ml HIb and 100% for 0.1 mg/ml Hb), with the NTA and EDTA 3 μm showing less binding of Hb (over 65% for 0.5 mg/ml Hb and 75% for 0.1 mg/ml Hb).

Detection of Captured HbA1c.

The silica EDTA and polystyrene NTA microparticles were coated with zinc and incubated at 0.5% solids with 0.1 mg/ml Hb spiked with 0, 1, 5 and 10% HbA1c. Particles were probed with α-HbA1c antibodies (10 ug/ml) and α-mouse-alkaline phosphatase (diluted 1:3000). After incubation with alkaline phosphatase substrate, the reaction was stopped and OD 550 nm was read.

TABLE 4

Silica EDTA and polystyrene NTA microparticles.

| | PBS (Blank) | 0.1 mg/ml Hb | Hb + 10% HbA1c |
| --- | --- | --- | --- |
| polystyrene NTA | 0.204 | 0.273 | 0.262 |
| Silica EDTA 1.5 μm (1st batch) | 0.207 | 0.323 | 0.412 |

TABLE 4-continued

Silica EDTA and polystyrene NTA microparticles.

| | PBS (Blank) | 0.1 mg/ml Hb | Hb + 10% HbA1c |
| --- | --- | --- | --- |
| Silica EDTA 1.0 μm | 0.298 | 0.44 | 0.49 |
| Silica EDTA 1.5 μm (2nd batch) | 0.199 | 0.383 | 0.412 |
| Silica EDTA 3.0 μm | 0.109 | 0.245 | 0.242 |

The silica EDTA 1-1.5 μm microparticles gave the best result, showing an increased signal with addition of 10% HbA1c.

Example 4

Use of Different Types of Zinc Coated Microparticles

Silica EDTA Microparticles

Microparticles were coated with zinc and resuspended in 40% sucrose prior to analysis by the IMX™ method described in Example 2.

TABLE 5

| Sample | Blank | Rate |
| --- | --- | --- |
| RBC (5% HbA1c) | 244 | 677 |
| RBC (9% HbA1c) | 244 | 746 |

The silica particles were able to bind HbA1c and successfully discriminated samples with 5 and 9% HbA1c.

Polystyrene EDTA Microparticles

Microparticles were coated with zinc and resuspended in 30% sucrose prior to analysis by the AXSYM™ method described in Example 1. The αHbA1c (2 μg/ml) was incubated for 5 mm followed by α-mouse-alkaline phosphatase (1:3000) for 2 mm.

TABLE 6

| Sample | Blank | Rate |
| --- | --- | --- |
| RBC (5% HbA1c) | 112 | 230 |
| RBC (9% HbA1c) | 162 | 494 |

The polystyrene EDTA microparticles were able to bind HbA1c and successfully discriminated samples with 5 and 9% HbA1c.

Polystyrene NTA Microparticles

Microparticles were coated with zinc prior to analysis by the vacuum manifold method described in Example 3.

TABLE 7

| | PBS (Blank) | 0.1 mg/ml Hb | Hb + 10% HbA1c |
| --- | --- | --- | --- |
| polystyrene NTA | 0.204 | 0.273 | 0.262 |

The polystyrene NTA microparticles were able to bind Hb but showed very low or almost no discrimination of HbA1c after spiking 10% HbA1c in the sample.

Magnetic Zn Microparticles

Microparticles were analyzed by vacuum manifold for binding capabilities, using the method described in Example 3.

TABLE 8

|  | Average OD 405 nm (−background) | Bound (%) |
| --- | --- | --- |
| Measured unbound 1.0 mg/ml Hb | 0.105 | 85 |
| Measured unbound 0.5 mg/ml Hb | 0.051 | 93 |
| Blank (HEPES buffer) | 0.048 | — |
| 0.5 mg/ml Hb | 0.695 |  |

Magnetic Zn microparticles successfully bound Hb.

The bound Hb was analysed for HbA1c using analysis by vacuum manifold (method described in Example 3).

TABLE 9

|  | Average OD 550 nm |
| --- | --- |
| 0.1 mg/ml Hb | 0.384 |
| Blank (HEPES buffer) | 0.194 |

The results indicate that magnetic Zn microparticles can be used to detect bound HbA1c.

Chelating Sepharose

Chelating sepharose was coated with zinc and incubated with lysed blood sample and analyzed using the vacuum manifold for binding capabilities method described in Example 3.

TABLE 10

| Sample | Unbound Hb (OD405 nm) | Bound Hb (OD405 nm after EDTA elution) |
| --- | --- | --- |
| Lysed RBC | 0.265 | 2.608 |

These results indicate that most of the hemoglobin was bound to the chelating sepharose.

Example 5

Use of Different Metal Ions

Chelating Sepharose

Chelating sepharose was coated with various metal ions and incubated with lysed blood sample, and was analyzed using the vacuum manifold for binding capabilities method described in Example 3.

TABLE 11

| Metal ion | Unbound Hb (OD405 nm) | Bound Hb (OD405 nm after EDTA elution) |
| --- | --- | --- |
| Zinc chloride | 0.265 | 2.608 |
| Nickel sulphate | 1.953 | 2.165 |
| Copper sulphate | 1.078 | 0.359 |
| Iron chloride | 3.667 | 0.290 |
| Non coated chelating sepharose | 2.361 | 0.695 |

These results indicate that zinc chloride bound the greatest quantity of hemoglobin.

Silica EDTA Microparticles

Silica EDTA microparticles were coated with various metal ions and analysed by IMX™ method described in Example 2.

TABLE 12

| Metal ion | Rate (−blank) |
| --- | --- |
| Zinc chloride | 443 |
| Iron chloride | 122 |
| Gold chloride | 91 |

These results indicate that zinc chloride bound the most HbA1c that could be detected by IMX™.

Example 6

Use of Detergent to Lyse RBC and Still Allow Binding and Detection of HbA1c on Zinc Coated Microparticles Experiment 1

Blood samples were lysed with buffer containing 0.5% TX100+0.8 mM zwittergent3-14 and analysed by the AXSYM™ method described in Example 1.

TABLE 13

| Sample | Rate (−Blank) |
| --- | --- |
| Normal (5% HbA1c) | 376 |
| High (9% HbA1c) | 568 |

Experiment 2

Blood samples were lysed with buffer containing 0.5% TX100+80 mM cholate and analysed by the AXSYM™ method described in Example 1.

TABLE 14

| Sample | Rate (−Blank) |
| --- | --- |
| Normal (5% HbA1c) | 20 |
| High (9% HbA1c) | 465 |

Experiment 3

Blood samples (normal, 5% HbA1c) were lysed with buffer containing 0.5% TX100+ various detergents and were analysed by the IMX™ method described in Example 2. The HbA1c was detected with αHbA1c-alkaline phosphatase (1 μg/ml) in blocking buffer 17.

TABLE 15

| Sample | Rate (−Blank) |
| --- | --- |
| 80 mM cholate | 840 |
| 250 mM N-octyl-glucoside | 807 |
| 90 mM N-octyl-thioglucoside | 395 |

These results indicate that the use of various detergents to lyse red blood cell membranes (RBC) does not affect the subsequent binding and detection of HbA1c bound to zinc coated EDTA microparticles.

Example 7

Capture of HbA1c on Various Sized Silica Microparticles and Use of Anti-HbA1c-Alkaline Phosphatase Conjugate for Detection Blood samples were lysed with lysis buffer containing 80 mM cholate and analysed by the IMX™ method described in Example 2, with only one incubation step with conjugate. Samples were incubated with silica microparticles of various sizes (1.5, 0.5 and 0.3 μm) at 0.05% solids. The HbA1c was detected with .αHbA1c-alkaline phosphatase (1 μg/ml) in Hepes pH 7.0. Sodium Azide 0.2%, 2% PEG 1000 and 1.2% STABILGUARD™ conjugate diluent.

TABLE 16

| Particles (um) | Blank | Rate | Rate − Blank | Rate:Blank Ratio |
|---|---|---|---|---|
| 1.5 | 93 | 1009 | 916 | 11:1 |
| 0.5 | 93 | 422 | 329 | 5:1 |
| 0.3 | 93 | 3329 | 3236 | 36:1 |

Example 8

Optimization of Conditions and Reagents for Performance of Automated Glycated Hemoglobin Quantification Using the AXSYM™ Automated Assay The optimization of the conditions for performance of the assays has resulted in the following protocol and buffers being identified as suitable for the performance using automated analysis on the AXSYM™ automated assay machine (Abbott Laboratories, US).

Performance of Assay Methodology

5 μl of whole blood sample (EDTA, FLUOX, citrate, heparin) was added to 95 μl of RBC lysis buffer (1/20 dilution). The lysed sample was further diluted with 100 μl of sample diluent (final sample dilution of 1/40).

Tab blocker (95 μl) was put on the AXSYM™ tab of the matrix cell with a 20 second delay. The diluted lysed sample (95 μA) was transferred to the tab and the tab was washed with 100 μl of AXSYM™ Solution 3 with a 10 second delay. Conjugate (90 μl) was added to the tab and incubated for 300 seconds. The tab was then washed with 2×100 μl of AXSYM™ Solution 3 with a 10 second delay between each pulse and 1×50 μl of MUP was put on the tab.

The fluorescent product was then read 8 times, with each read taking 506.88 msec and 0.6 seconds between each read. The gain was set at 20. Time to first result was 13.7 with a throughput of 46 tests per hour.

The buffers for use in the methods of this example are formulated as follows:

(i) Working Strength Conjugate

DAKO™ mouse anti-Hb(A,C,S)1c and anti-HbA1c have been conjugated in-house with alkaline phosphatase using convential maleimide conjugation procedures. They were evaluated and anti-Hb(A,C,S)1c alkaline phosphatase conjugate performed best. The conjugate is used at 0.25 μg/ml concentration in conjugate diluent (buffer formulation is 0.05M HEPES, 6% STABILGUARD™, 2% polyethylene 1000, 0.5% Triton-X100, 1% StabilzymeAP, 0.09% sodium azide, pH 7).

(ii) RBC Lysis Buffer

Best performance was achieved using 0.2M HEPES, 0.055M Glycine, 0.05M magnesium chloride, 0.4M sodium choride, 1% Triton-X100, 0.8 mM Zwittergent 3-14, 0.09% Sodium Azide, pH 8.

(iii) Tab Blocker/Sample Diluent

Variation of AXSYM™ matrix cells was minimized and Hb binding was optimal when a tab blocker and sample diluent were used. The two buffers used were buffer 3 (0.05M Tris, 20% sucrose, 0.5M sodium chloride, 0.1% fish skin gelatin, 10% STABILGUARD™, 1 mM zinc chloride, 0.09% sodium azide, pH 8) and buffer 7 (0.05M Tris, 20% sucrose, 2M sodium chloride, 0.1% fish skin gelatin, 16% STABILGUARD™, 5% polyethylene glycol 8000, 0.1% casein hydrolysate, 1 mM zinc chloride, 0.09% Sodium Azide, pH 8).

All documents referred to in this specification are herein incorporated by reference. While the present disclosure has been described in connection with the examples discussed above and the various figures, it is to be understood that other similar examples may be used, or modifications or additions may be made to the described examples for performing the same function without deviating therefrom. Therefore, the present disclosure should not be limited to any single example, but rather should be construed in breadth and scope in accordance with the recitation of the appended claims.

We claim:

1. An assay method for determining the level of glycated hemoglobin within a sample, comprising:
   providing a sample comprising hemoglobin;
   denaturing the hemoglobin to effect a conformational change which causes exposure of a zinc binding site;
   capturing the hemoglobin using zinc coupled to a support medium; and
   determining the amount of glycated hemoglobin bound by the coupled zinc.

2. The assay method of claim 1, wherein denaturation is caused by detergents.

3. The assay method of claim 1, wherein the detergents are one or more of the detergents selected from the group consisting of cholate, N-octyl-glucoside, N-octyl-thioglucoside, triton X-100, zwittergent3-14 and bile salts.

4. The assay method of claim 1, wherein capture of the hemoglobin by the coupled zinc is performed in the presence of detergent.

5. The assay method of claim 1, wherein the support medium is a microparticle.

6. The assay method of claim 5, wherein the microparticle is a bead selected from the group consisting of a latex bead, a polystyrene bead, a silica bead, a chelating sepharose bead and a magnetic bead.

7. The assay method of claim 5, wherein the zinc is provided by zinc chloride.

8. The assay method of claim 5, wherein the microparticle comprises dextran or polyethylene glycol.

9. The assay method of claim 1, wherein a chelator facilitates the coupling of the zinc to the support medium.

10. The assay method of claim 9 wherein the chelator is a zinc binding chelating agent.

11. The assay method of claim 9, wherein the chelator is selected from the group consisting of ethylenediamine tetraacetic acid, trisodium calcium diethylenetriamin-pentaacetate, disodium calcium cyclohexanediaminetetraacetate, sodium calcium edetate, DMSA, DMPS, ethylenediamine, diethylenetriamine, aminoethylethanol amine ethyleneamines and combinations thereof.

12. The assay method of claim 1, wherein the sample comprises whole blood, red blood cells, blood hemolysates or blood extracts.

13. The assay method of claim 12, wherein the sample comprises whole blood cells which are lysed prior to denaturation.

14. The assay method of claim 12, wherein the sample comprises red bloods cells which are lysed using detergents.

15. The assay method of claim 12, wherein the sample comprises red bloods cells which are lysed using heat.

16. An assay method for the determination of the level of glycated hemoglobin within a sample, comprising:
    providing a blood sample;
    extracting the hemoglobin from the sample and partially denaturing the hemoglobin;
    exposing the hemoglobin to microparticles coated with zinc to allow binding of hemoglobin and glycated hemoglobin to the microparticles; and
    determining the amount of glycated hemoglobin bound to the microparticles.

17. The assay method of claim 16, wherein hemoglobin is extracted from the sample by hemolysis of the sample to release cell bound hemoglobin.

18. The assay method of claim 16, wherein the partial denaturation of the hemoglobin during the treatment step is performed with detergents.

19. The assay method of claim 18, wherein the detergents are one or more of the detergents selected from the group consisting of cholate, N-octyl-glucoside, N-octyl-thioglucoside, triton X, zwittergent3-14 and bile salts.

20. The assay method of claim 16, wherein the step of exposing the hemoglobin to the zinc coated microparticles is performed at a pH of about 7.

21. The assay method of claim 16, wherein the determination of the amount of glycated hemoglobin present is performed by contacting the glycated hemoglobin with signal-generating molecules which selectively bind to glycated hemoglobin.

22. An assay method for the in-vitro diagnosis and monitoring of diabetes mellitus through the assessment of glycated hemoglobin levels, the method comprising:
    providing a blood sample;
    hemolysing the blood sample to release cell bound hemoglobin and partially denature the hemoglobin;
    capturing glycated hemoglobin on microparticles coated with zinc;
    exposing the captured glycated hemoglobin on the microparticles to signal generating molecules which bind to the glycated hemoglobin;
    removing signal generating molecules not bound to glycated hemoglobin; and
    quantifying the amount of bound signal generating molecules to determine the percentage level of glycated hemoglobin present in the sample.

23. The assay method of claim 22, wherein the step of determining the percentage level of glycated hemoglobin present in the sample comprises:
    capturing the microparticles on a suitable base medium;
    washing the microparticles to remove unbound material; and
    labelling the glycated hemoglobin with a signal generating molecule comprising a monoclonal antibody specific for glycated hemoglobin, the monoclonal antibody having a label conjugated thereto.

24. A method of isolating hemoglobin from a biological sample, the method comprising:
    providing a biological sample;
    capturing the hemoglobin on microparticles which are coated with zinc; and
    eluting the microparticle-bound hemoglobin from the zinc coated microparticles.

25. The method of claim 24, further comprising the step of hemolysing the sample and partially denaturing the hemoglobin present in the sample prior to the capturing step.

26. The method of claim 24, wherein the biological sample comprises blood.

27. The method of claim 24, wherein the amount of glycated hemoglobin present in the sample is quantified.

28. An assay for the selective binding of at least one target protein bearing a zinc binding site, comprising:
    providing a sample;
    exposing the sample to zinc coated microparticles;
    capturing the target proteins on the zinc coated microparticles;
    isolating the microparticles;
    detecting the presence of target proteins bound to the microparticles; and
    optionally purifying the target protein from the microparticles.

29. The assay method of claim 28, wherein the sample is a biological sample.

30. A kit comprising zinc-coated microparticles and instructions for the performance of the assay method of claim 1.

* * * * *